United States Patent [19]

Clark et al.

[11] 3,959,314

[45] May 25, 1976

[54] PREPARATION OF 2-ARYL-2-HYDROXYIMINOACETIC ACIDS (SYN ISOMERS)

[75] Inventors: Victor Malcolm Clark, Coventry; Gordon Ian Gregory, Chalfont St. Peter; Godfrey Basil Webb, Greenford, all of England

[73] Assignee: Glaxo Laboratories Limited, Greenford, England

[22] Filed: Feb. 14, 1974

[21] Appl. No.: 442,401

[30] Foreign Application Priority Data

Feb. 20, 1973 United Kingdom.............. 8382/73

[52] U.S. Cl..................... 260/332.2 A; 260/295 R; 260/307 R; 260/347.3; 260/516; 260/518 A; 260/519
[51] Int. Cl.$^2$........................................ C07D 333/24
[58] Field of Search................ 260/332.2 A, 295 R, 260/307 R, 518 R

[56] References Cited

OTHER PUBLICATIONS

Edge et al., "Chemical Abstracts," p. 77108w, Vol. 70, (1969).

Ahmad et al., "Canadian J. Chemistry," 39, 1340 (1961).

Primary Examiner—James O. Thomas, Jr.
Assistant Examiner—A. Siegel
Attorney, Agent, or Firm—Bacon & Thomas

[57] ABSTRACT

2-Aryl-2-hydroxyiminoacetic acids rich in the syn isomer are prepared by reaction of an arylglyoxylic acid with hydroxylamine in an aqueous reaction medium, e.g. water, in the presence of a source of magnesium, calcium or zinc ions, e.g. magnesium hydroxide. The acids so obtained are of value as synthetic intermediates in the preparation of penicillin and cephalosporin antibiotics containing syn-2-aryl-2-hydroxyiminoacetamido side chains.

8 Claims, No Drawings

PREPARATION OF 2-ARYL-2-HYDROXYIMINOACETIC ACIDS (SYN ISOMERS)

This invention relates to the preparation of 2-aryl-2-hydroxyiminoacetic acids.

2-Aryl-2-hydroxyiminoacetic acids are important intermediates in, for example, the preparation of 7β-acylamido cephalosporins and 6β-acylamido penicillins in which the acyl group is derived from such acids. Cephalosporins and penicillins of this type are described, for example, in our Belgian Pat. No. 778,630.

2-Aryl-2-hydroxyiminoacetic acids and cephalosporin and penicillin compounds containing acyl groups derived therefrom exist in syn and anti isomeric forms depending on the configuration of the hydroxyimino group with respect to the carboxyl or carbonyl group. The syn isomeric forms of cephalosporins and penicillins of this type and mixtures of the syn and anti forms in which the syn form predominates, are of particular value on account of their high antibacterial activity and stability to β-lactamases.

In this Specification the prefix syn is used with reference to compounds including the structure

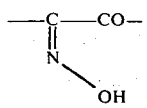

while the prefix "anti" is used with reference to compounds including the structure

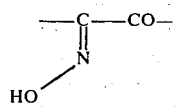

These configurations are assigned on the basis of the work of Ahmad and Spenser reported in Can. J. Chem., 39, 1340 (1961).

One method of preparing 2-aryl-2-hydroxyiminoacetic acids involves reaction of an arylglyoxylic acid with hydroxylamine. The ratio of syn and anti isomers in the product of this reaction is influenced to some extent by the structure of the starting arylglyoxylic acid and also by such factors as the reaction medium, pH, reactant concentrations and stoichiometry. Thus, for example, the anti isomer tends to predominate when the reaction is conducted at alkaline pH, e.g. at a pH greater than or equal to about 11.

It is desirable when preparing syn forms of the 2-aryl-2-hydroxyiminoacetic acids for the proportion of the anti form produced to be reduced as far as possible, or eliminated altogether. While the proportion of the anti isomer in a reaction product may be reduced to some extent by careful selection of reaction conditions such as pH, we have not found it possible in this way to reduce the anti isomer content of the total reaction product to an acceptable level using known preparative methods, and there is thus a need for processes yielding 2-aryl-2-hydroxyiminoacetic acids containing a substantially lower proportion of the anti isomer.

According to the present invention there is provided a process for the preparation of a 2-aryl-2-hydroxyiminoacetic acid rich in the syn isomer which comprises reacting an arylglyoxylic acid with hydroxylamine in an aqueous reaction medium in the presence of a source of magnesium, calcium or zinc ions.

Test results show that use of these reaction conditions, especially reaction in the presence of magnesium ions, leads to the formation of a 2-aryl-2-hydroxyiminoacetic acid product in which the syn : anti isomer ratio is significantly improved in favour of the syn form with the anti form being produced in only small amounts, e.g. 5 – 10%.

The arylglyoxylic acid used as starting material in the process of the invention may be represented by the general formula

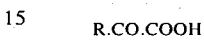

where R is aryl (carbocyclic or heterocyclic) or substituted aryl.

The resulting 2-aryl-2-hydroxyiminoacetic acid may similarly be represented by the formula

where R has the above-defined meaning.

In these formulae, the group R is preferably monocyclic, suitable groups thus including phenyl; substituted phenyl, for example phenyl substituted by halo (e.g. chloro or bromo), hydroxy, lower alkyl (e.g. containing 1 – 6 carbon atoms, such as methyl), nitro, amino, lower alkylamino (e.g. methylamino), di(lower alkyl)amino (e.g. dimethylamino), lower alkanoyl (e.g. acetyl), lower alkanoylamide (e.g. acetamido), lower alkoxy (e.g. methoxy or ethoxy), or lower alkylthio (e.g. methylthio); and 5- or 6-membered heterocyclic groups containing heteroatoms selected from S, N and O, e.g. thienyl, furyl, pyridyl or oxazolyl. Preferred R groups include phenyl; thien-2-yl, thien-3-yl,fur-2-yl and fur-3-yl. The arylglyoxylic acid may, if desired, be added to the reaction system in the form of a salt, e.g. an alkali metal salt such as the sodium or potassium salt.

The source of magnesium, calcium or zinc ions is conveniently the appropriate metal hydroxide or oxide; we particularly prefer to use magnesium hydroxide. Alternatively, salts, e.g. chlorides or bromides, of these metals may be employed.

The hydroxylamine required in the reaction is conveniently added in the form of an acid addition salt, e.g. the hydrochloride or sulphate.

The hydroxylamine is desirably used in slight excess in relation to the arylglyoxylic acid. A mole ratio of 1:1 to 2:1 is suitable, the preferred mole ratio being about 1.2:1. The source of magnesium, calcium or zinc ions is desirably used in somewhat greater excess in relation to the arylglyoxylic acid, e.g. in a mole ratio of up to 10:1. Mole ratios of 2–5:1 are preferred, particularly when the source of the metal ions is a metal hydroxide or oxide.

The aqueous reaction medium employed in the process may, for example, be water itself. In view of the relatively low solubility in water of the hydroxides and oxides of magnesium, calcium and zinc the reaction is usually heterogeneous in order to achieve desirable concentrations of the metal ions. Co-solvents may be used together with water, suitable examples being cyclic ethers such as dioxan or tetrahydrofuran, and alcohols, e.g. lower alkanols such as methanol and ethanol.

The reaction is conveniently carried out without the application of external heat. In general, temperatures ranging from the freezing point of the medium up to reflux, e.g. 0°–100°C, may be used. At 20°C the reaction is generally virtually complete in 2–4 hours, but in some circumstances the reaction mixture may be left for longer periods to ensure that the consumption of the arylglyoxylic acid is maximised, thus simplifying the purification of the product.

The reaction may be effected at a pH of about 5.5–13, the optimum pH depending on the source of magnesium, calcium or zinc ions which is employed and on the other reaction conditions. Where the source of the metal ions is an oxide or hydroxide, satisfactory results may be obtained without taking any special steps to control the pH of the reaction medium. Thus, for example, when using an arylglyoxylic acid: hydroxylamine hydrochloride: magnesium hydroxide mole ratio of 1:1.2:5, in water, the pH is about 9. This does of course vary as the reaction proceeds and the hydroxylamine is consumed, and it may therefore be advantageous to control the pH.

The 2-aryl-2-hydroxyiminoacetic acid produced in the reaction may be isolated from the reaction mixture by any convenient technique, for example by acidifying the reaction mixture with an excess of a strong mineral acid (e.g. having a pKa of 2 or less) such as hydrochloric acid relative to the quantity of metal ions present and extracting the product with an organic solvent, e.g. a di(lower alkyl) ether such as diethyl ether or di-isopropyl ether. The acidification is preferably carried out at as low a temperature as possible (e.g. at about 5°C) and is desirably conducted in the presence of the said organic solvent so that the product is extractively removed from the aqueous reaction mixture as quickly as possible, thus minimising isomerisation of the syn isomer to the anti isomer.

The following examples illustrate the invention. Temperatures are in °C.

EXAMPLE 1

Syn-2-Hydroxyimino-2-(thien-2-yl)acetic acid

A solution of thien-2-ylglyoxylic acid (15.6g) in warm water (250 ml.) was cooled to room temperature and treated with magnesium hydroxide (29.0g). To the vigorously stirred suspension was added a solution of hydroxylamine hydrochloride (8.4g) in water (25 ml.). The flask was stoppered and the suspension was stirred for 18 hrs. The mixture was cooled to 0° and concentrated hydrochloric acid added dropwise to pH 1 with stirring. The mixture was covered with ether, a small excess of hydrochloric acid was added and the aqueous layer was then extracted three times with ether. The extracts were washed with brine, dried and evaporated to dryness. The solid product, dried in vacuo over silica gave the title compound (16.74g; 98%) m.p. 129.9° (dec.); $\lambda_{Max}^{EtOH}$ 285 nm. ($\epsilon$ 9,100);$\tau$ (DMSO-d6) values include 2.4 (m,1H) and 2.85 (m, 2H); and a signal at 2.15 (m,2H) diagnostic for and equivalent to 5–10% anti-isomer.

EXAMPLE 2

Syn-2-Hydroxyimino-2-(thien-2-yl)acetic acid

A solution of thien-2-ylglyoxylic acid (15.6g) was treated as in Example 1 using magnesium hydroxide (11.8g) in an otherwise identical reaction. The product (16.77 g; 98%) had m.p. 127.6° (dec.) and was estimated to be 90% syn isomer and 10% anti-isomer by p.m.r. analysis.

EXAMPLE 3

Syn-2-Hydroxyimino-2-(fur-2-yl)acetic acid

To a solution of fur-2-ylglyoxylic acid (42 g.) in water (600 ml.) was added magnesium hydroxide (35.8g) followed by a solution of hydroxylamine hydrochloride (25.2g) in water (150 ml.). After stirring at room temperature for 2½ hrs, ether (300 ml.) was added followed by 2N-hydrochloric acid (450 ml.). The aqueous phase was saturated with sodium chloride, separated and twice extracted with ether. The combined ether extracts were dried and the solvent evaporated to give an oil which was seeded with an authentic sample of the title compound to produce a solid. The solid was triturated with petroleum spirit (bp. 60°–80°) filtered, washed with petroleum spirit (bp. 60°–80°) and dried in vacuo to give the title compound (40.5g; 87%) m.p. 122.5° (dec.); $\lambda_{Max}^{EtOH}$ 272.5 nm. ($\epsilon$11,800) $\tau$ values (DMSO-d6) include 2.15 (m, 1H) and 3.3 (m,2H) and a signal at 2.65 (m,1H) diagnostic for and equivalent to ca. 5% of the anti-isomer.

EXAMPLE 4

Syn-2-Hydroxyimino-2-phenylacetic acid

Magnesium hydroxide (146 g.) was added to a solution of phenylglyoxylic acid (75 g.) in water (750 ml.) and to this stirred suspension was added a solution of hydroxylamine hydrochloride (41.7g) in water (100 ml.). The mixture was stirred for 2.5 hrs., cooled in an ice bath then acidified to pH 1.5 under ether with concentrated hydrochloric acid. The acid solution was extracted with ether, and the combined ether extracts were washed (water, saturated brine), dried, and evaporated to dryness to give the title compound (80.4g; 97.5%) m.p. 128.1°. The purity of the acid was determined by conversion into its methyl ester using etheral diazomethane and comparing the p.m.r. spectrum with those of authentic samples of syn and anti-methyl 2-hydroxyiminophenylacetates. $\tau$ Values (CDCl$_3$) include 6.05 (syn,O—CH$_3$) (ca. 98%) and 6.14 (anti, OCH$_3$) (ca. 2%).

EXAMPLE 5

Syn-2-Hydroxyimino-2-(thien-3-yl)acetic acid

Magnesium hydroxide (5.6g) was added to a solution of thien-3-ylglyoxylic acid (3.01 g.) in water (50 ml.) and to the resulting stirred suspension was added a solution of hydroxylamine hydrochloride (1.61 g.) in water (10. ml.). The mixture was stirred for 3 hrs. then acidified to pH 1.5 under ether. The resulting solution was extracted with ether, and the combined ether extracts were washed (water, saturated brine) dried, and evaporated to dryness to give the title compound (2.88 g 87%) ca. 95% syn isomer estimated by p.m.r. spectroscopy. The above solid was stirred with methylene chloride (25 ml.) to give almost pure syn-2-hydroxyimino-2-(thien-3-yl)acetic acid (2.33 g.) m.p. 132.4°–133.1°; λ max (ethanol) 253 nm. ($\epsilon$ 11,300), $\tau$ values, (DMSO-d6) include 2.40 and 2.63 (thienyl protons), and a signal at 1.78 diagnostic for and equivalent to ca. 2% anti-isomer.

EXAMPLE 6

Syn-2-Hydroxyimino-2-(fur-2-yl)acetic acid

To a stirred solution of fur-2-ylglyoxylic acid (1.4 g.) in water (25 ml.) was added zinc oxide (1.63 g.) followed by a solution of hydroxylamine hydrochloride (0.84 g.) in water (5 ml.). After stirring at room temperature for 3 hours the reaction mixture was poured into 2N-hydrochloric acid (20 ml.) covered with ether. The mixture was saturated with salt and extracted three times with ether. Evaporation of the dried extracts gave the title compound (1.338g; 86%) m.p. 118.9° (dec) estimated to contain 10% of the anti-isomer by p.m.r. analysis as described in Example 3.

EXAMPLE 7

Syn-2-Hydroxyimino-2-(thien-2-yl)acetic acid

To a stirred solution of thien-2-ylglyoxylic acid (1.56 g.) in water (30 mml.) was added calcium hydroxide (3.7 g) followed by a solution of hydroxylamine hydrochloride (0.84 g) in water (15 ml). After stirring at room temperature for 4¼ hours the mixture was cooled in an ice-bath then acidified to pH 1 under ether with dilute hydrochloric acid. The acid solution was extracted with ether and the combined ether extracts washed with brine, dried, and evaporated to dryness. The product (1.56g; 91%) had m.p. 128.4° (dec); it was estimated to be 80% syn-isomer and 20% anti isomer by p.m.r. analysis as described in Example 1.

EXAMPLE 8

Syn-2-Hydroxyimino-2-(fur-3-yl)acetic acid

Magnesium hydroxide (3.58 g) was added to a solution of fur-3-ylglyoxylic acid (4.2 g) in water (100 ml) and the mixture stirred at room temperature for 15 minutes. A solution of hydroxylamine hydrochloride (2.52g) in water (15 ml) was added and the suspension stirred for 3 hours. The mixture was cooled in an ice-bath and acidified to pH 1 under ether with concentrated hydrochloric acid. The ether layer was separated and the aqueous layer saturated with salt and extracted with ether. The combined ether extracts were washed with brine, dried and evaporated to dryness to give the title compound (4.3g; 92%) m.p. 147.3° (dec.); $\lambda_{inf.}^{EtOH}$ 227 nm ($\epsilon$, 6,900) $\tau$ values (DMSO-d6) include 2.09 (broad s, 1H), 2.22 (m, 1H), 3.29 (m, 1H) (indicating ca. 85% syn-ismer) and 2.96 (m, 1H) diagnostic for and equivalent to ca. 15% of the anti-isomer.

The fur-3-ylglyoxylic acid used in this example was prepared as follows:

To a stirred solution of 3-acetylfuran (13g) in pyridine (20 ml) at 60° was added selenium dioxide (19 g). The mixture was stirred mechanically and heated gradually to 100° when an exothermic reaction occurred. The heating was removed until the reaction mixture which reached 120° had cooled to 90° (ca 10 min.) and was then maintained at 90° for 1 hr. The reaction mixture was cooled to room temperature, diluted with water (70 ml) and filtered through a kieselguhr bed. The filtrate was extracted with ether and the extract discarded. The aqueous phase was acidified to pH 2.0 with 40% phosphoric acid (100 ml) and extracted with ether. The aqueous phase was saturated with salt and extracted twice more with ether. The combined ether extracts were washed with brine, dried and evaporated to dryness affording a yellow crystalline solid (12.3 g: 73%). A sample (500 mg) of the product crystallised from benzene to give yellow crystals (300 mg) of fur-3-ylglyoxylic acid m.p. 94.2°; $\lambda_{max}^{EtOH}$ 224.5, 284 nm ($\epsilon$, 4,850; 3,150); $\tau$ (DMSO-d6) values 1.23 (m, 1H), 2.04 (m, 1 H) and 3.07 (m, 1 H). The remaining crude product crystallised from benzene as two crops (5.48 g) m.p. 94.2° and (2.69g) m.p. 93.7°.

EXAMPLE 9

Syn-2-Hydroxyimino-2-(thien-2-yl)acetic acid

A mixture of thien-2ylglyoxylic acid (937g) and water (9.0 liters) was stirred for 20 minutes. Magnesium hydroxide (700g) was added portionwise over 10 minutes. The mixture was stirred for a further 20 minutes whereafter a solution of hydroxylamine hydrochloride (500g) in water (1.5 liters) was added over 40 minutes. The reaction mixture was stirred for 16 hours at room temperature and then cooled to 0°. Hydrochloric acid (5N; ca 2.4 liters) was added over 45 minutes until a steady pH of 1.2 was obtained. The mixture was filtered through a Kieselguhr bed and washed by displacement with hydrochloric acid (2N:1.2 liters). The combined filtrate and wash were covered with isopropyl ether (5 liters) and stirred whilst hydrochloric acid (5N:ca 480 ml) was added. The two phases were allowed to separate and the aqueous phase re-extracted with isopropyl ether (1 × 3 liters: 2 × 1.5 liters). The first three isopropyl ether extracts were combined and washed with saturated sodium chloride solution (3 × 3 liters), each wash itself being extracted with a fourth isopropyl ether extract. The combined organic extracts were stirred with anhydrous magnesium sulphate (250g) and charcoal (50g) for 10 minutes, filtered through a Kieselguhr bed and washed by displacement with isopropyl ether (1.5 liters). With stirring the extract was concentrated in vacuo in a hot water bath (50°) to a low bulk then reconcentrated twice (2 × 2 liters) from 1,2-dichloroethane. The concentrate was slurried at 0° with 1,2-dichloroethane (2 liters), filtered, and the bed washed with 1,2-dichloroethane (1 liter). The product was dried in vacuo at 40° to give the title compound (870g:84.5%) m.p. 129° (dec), estimated to contain <5% of the anti-isomer by p.m.r. analysis as described in Example 1.

EXAMPLE 10

Syn-2-Hydroxyimino-2-(4-hydroxyphenyl)acetic acid.

Magnesium hydroxide (3.8g) was suspended in a solution of 4-hydroxyphenylglyoxylic acid (2.0g) in water (30ml) and a solution of hydroxylamine hydrochloride (1.3g) in water (5ml) was added. The mixture was stirred at room temperature for 6 hrs, cooled in ice and acidified to pH 1.5 under ethyl acetate with 6N HCl. The acidic layer was saturated with NaCl and extracted twice with ethyl acetate. The combined ethyl acetate extracts were washed three times with brine, dried, and evaporated almost to dryness. Addition of dichloromethane gave a buff-coloured solid which was collected, washed with dichloromethane and dried in vacuo to give the title compound (1.66g, 76%) mp 128°–9°; $\lambda_{max}^{(EtOH)}$ 267.5 nm ($\epsilon$12,500).

We claim:

1. In a process for the preparation of an acid of the formula R.C(:NOH).COOH where R is phenyl; phenyl substituted by halo, hydroxy, lower alkyl, nitro, amino, lower alkyl amino, di(lower alkyl)amino, lower alkanoyl, lower alkanoylamido, lower alkoxy or lower alkylthio; thienyl; furyl; pyridyl or oxazolyl by reacting an acid of the formula R.CO.COOH where R has the meaning given above with hydroxylamine in an aqueous reaction medium, the improvement which comprises effecting the reaction at a temperature of 0°C.–100°C. and at a pH within the range of about 5.5–13, in the presence of a source of magnesium ions.

2. A process as claimed in claim 1 wherein the acid which is reacted is phenylglyoxylic acid, a thienylglyoxylic acid or a furylglyoxylic acid.

3. A process as claimed in claim 1 wherein the hydroxylamine and the glyoxylic acid are used in a mole ratio in the range 1:1–2:1.

4. A process as claimed in claim 3 wherein the hydroxylamine and the glyoxylic acid are used in a mole ratio of about 1.2:1.

5. A process as claimed in claim 1 wherein the source of magnesium ions and the glyoxylic acid are used in a mole ratio in the range 2:1–5:1.

6. A process as claimed in claim 1 wherein the source of magnesium ions is magnesium oxide or magnesium hydroxide.

7. In a process for the preparation of an acid of the formula R.C(:NOH).COOH where R is phenyl; phenyl substituted by halo, hydroxy, lower-alkyl, nitro, amino, lower alkyl amino, di(lower alkyl)amino, lower alkanoyl, lower alkanoylamido, lower alkoxy or lower alkylthio; thienyl; furyl; pyridyl or oxazolyl by reacting an acid of the formula R.CO.COOH where R has the meaning given above with hydroxylamine in an aqueous reaction medium, the improvement which comprises effecting the reaction at a temperature of 0°C.–100°C. and at a pH within the range of about 5.5–13, in the presence of a source of zinc ions.

8. A process as claimed in claim 7 wherein the source of said zinc ions is zinc oxide or zinc hydroxide.

* * * * *